United States Patent [19]

Fehrenbach et al.

[11] Patent Number: 4,816,687

[45] Date of Patent: Mar. 28, 1989

[54] METHOD AND APPARATUS FOR MEASUREMENT OF THE FLUORESCENCE RELAXATION PERIOD OF A FLUORESCENT SUBSTANCE

[75] Inventors: Gustav Fehrenbach, Hanau; Wolfgang Schäfer, Grosskrotzenburg, both of Fed. Rep. of Germany

[73] Assignee: Degussa AG, Frankfurt am Main, Fed. Rep. of Germany

[21] Appl. No.: 18,248

[22] Filed: Feb. 24, 1987

[30] Foreign Application Priority Data

Feb. 21, 1986 [DE] Fed. Rep. of Germany ....... 3605598
Oct. 6, 1986 [DE] Fed. Rep. of Germany ....... 3634045

[51] Int. Cl.$^4$ .......................... G01K 11/20; G01J 3/30
[52] U.S. Cl. .................................. 250/459.1; 356/311
[58] Field of Search .......................... 250/458.1, 459.1; 356/311; 374/131, 161, 162

[56] References Cited

U.S. PATENT DOCUMENTS

Re. 31,832  2/1985  Samulski .................. 250/459.1 X
4,296,318  10/1981  Mezzetti et al. ............... 374/161
4,652,143  3/1987  Wickersheim et al. ...... 250/459.1 X

OTHER PUBLICATIONS

Grattan et al., "Fire-Optic Absorption Temperature Sensar Using Fluorescence Reference Channel", Rev. Sci. Instrum., vol. 57, No. 6, Jun. 1986, pp. 1175-1178.

Primary Examiner—Gene Wan
Attorney, Agent, or Firm—Beveridge, DeGrandi & Weilacher

[57] ABSTRACT

The subject of the present invention consists of a method and an apparatus for measurement of the fluorescence relaxation period of the radiation of a fluorescent substance whose fluorescence relaxation period is a function of at least one physical parameter. The fluorescence radiation is fed back to the output radiation in a regulating circuit, whose regulating parameter is a parameter for the physical parameter. This is accomplished by advancing the fluorescence radiation to a photoelectric receiver whose output signals are supplied to a voltage controlled oscillator following phase-sensitive rectification and integration. The fluorescence radiation is alternately phase-sensitively rectified only during the relaxation phase. The total durations of the different rectification periods in the two directions are identical. The alternatingly rectified signals are integrated.

14 Claims, 7 Drawing Sheets

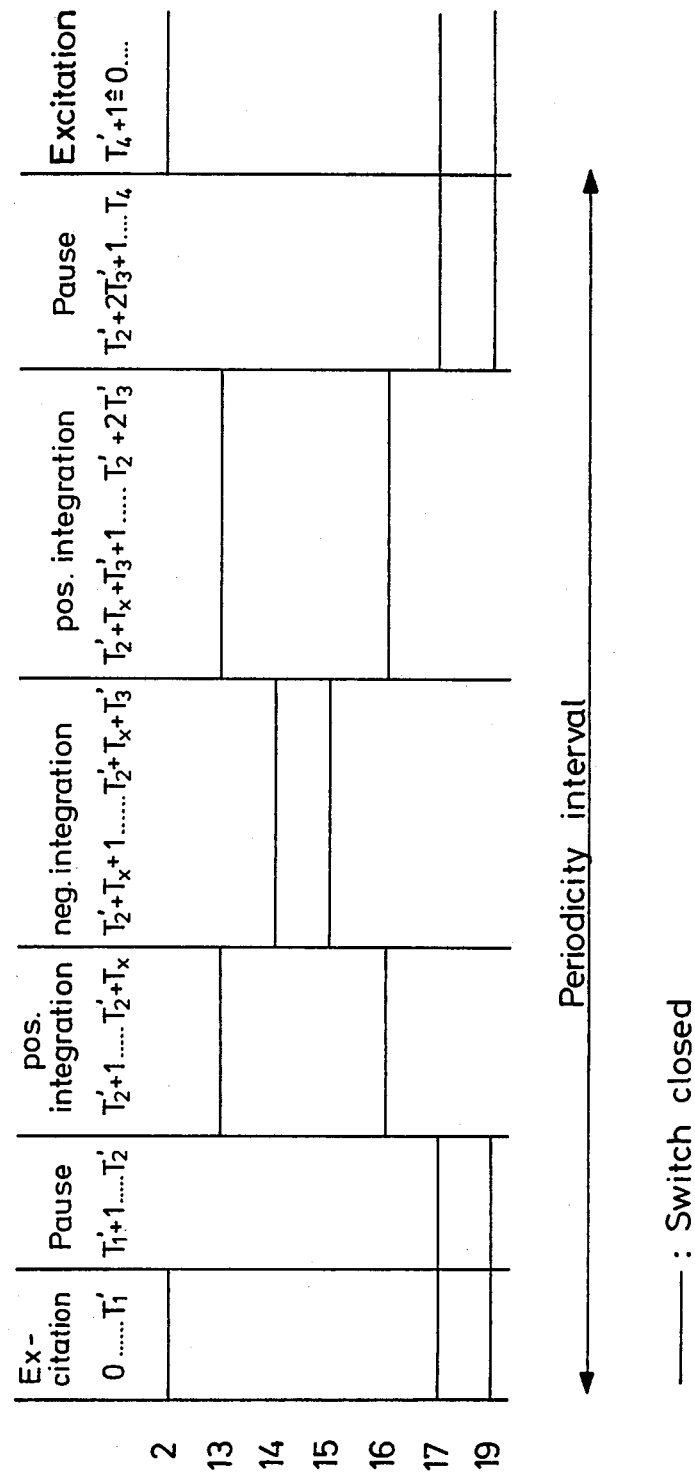

METHOD AND APPARATUS FOR MEASUREMENT OF THE FLUORESCENCE RELAXATION PERIOD OF A FLUORESCENT SUBSTANCE

BACKGROUND OF THE INVENTION

The present invention relates to a method and to apparatuses for measurement of the fluorescence relaxation period of the radiation of a fluorescent substance whose fluorescence relaxation period is dependent upon at least one physical parameter, in which the substance is subjected to radiation that is repeated at intervals of time, the radiation producing fluorescence radiation which is advanced to a photoelectric receiver whose output signals are phase-sensitively rectified and integrated and influence the regulating parameter of a regulating circuit, whose regulating parameter is a parameter for the physical parameter.

A fiber optic temperature sensor is known in which the fluorescent radiation is excited by a sinusoidally modulated radiator. The signal that is obtained from the delayed fluorescent light is fed back to the control means of the modulator via a timing element. The frequency to be set in the self-exciting oscillation circuit is a function of the fluorescence relaxation period, and thus of all physical parameters that influence this period (German Disclosed Patent Application No. 3,202,089). If the output signal of the photoelectric receiver is integrated during the excitation phase and the relaxation phase of the fluorescence radiation, measures are required for suppression of the crosstalk of the excitation source and for control of the curve of the excitation over time. It is necessary for optical filters and electronic stray light compensation means to be employed.

SUMMARY OF THE INVENTION

It is the object of the present invention to further develop a method of the type described at the outset for measurement of the physical parameter in such a manner as to eliminate impairment of the measurement accuracy as a result of crosstalk of an excitation channel, as a result of D.C. drifts, and as a result of slowly changing losses on a transmission link.

According to the present invention, this object is solved in that the fluorescence radiation is alternately phase-sensitively rectified only during the relaxation phase, in that the total periods of the differing rectification periods in the two different directions are identical, in that the alternately phase-sensitively rectified signals are integrated, and in that the sum of the integrals influences the oscillation of an oscillation circuit which generates the radiation in both directions, with the fluorescence radiation being fed back to the radiation. A further solution of the object according to the present invention is to emit the radiation in the form of an oscillation having a uniform or virtually uniform frequency, to alternately phase-sensitively rectify the fluorescence radiation only during the relaxation phase, and to have the regulating parameter consist of the relative durations of at least two rectification periods in both different directions, which are altered in such a manner that the sum of the integrals in both directions is zero or virtually zero.

The difficulties that exist in the prior art can be eliminated if the output signal of the photoelectric receiver is phase-sensitively rectified and integrated only outside the excitation phases of the fluorescence radiation. The method according to the present invention is thus crosstalk-neutral. The effort that is required in order to eliminate the influence of crosstalk is greatly reduced. A further particular advantage of the present invention is the fact that slowly changing losses on an optical waveguide link are eliminated.

In an especially practical embodiment of the present invention, clock pulses of uniform or virtually uniform frequency are counted during a period of the oscillation and are compared with stipulated values for the excitation phase and the rectification periods for the purpose of generating control signals, with the durations of the rectification periods being decreased or increased as a function of the positive or negative result of the integration and then outputted. The time at which rectification is reversed is a clear function of the relaxation period. This can easily be determined if the interrelationship that exists between the relaxation period and a physical parameter that is to be measured is known. Although it is especially advantageous to employ the teachings according to the present invention for fiber optic temperature sensors, it should be understood that the employment of the present invention is not restricted to this specific application.

BRIEF DESCRIPTION OF THE DRAWINGS

The above discussed and other objects, features and advantages of the present invention will become more apparent from the following description thereof, when taken in connection with the practical examples shown in the accompanying drawings, in which

FIG. 7 shows a time diagram of control signals for switches according to the apparatus illustrated in FIG. 6.

DETAILED DESCRIPTION OF THE PREFERRED EMBODIMENTS

In the case of simple exponential relaxations, the intensity curve over time following excitation can be described by means of the following equation:

$$I(t) = I_o e^{-t/\tau},$$

where I is the intensity of the radiation, Io the original intensity thereof and $\tau$ the luminescence relaxation period.

It is not possible to suppress the D.C. drift by means of phase-sensitive rectification, e.g. with symmetrical intervals of time $\Delta T$, as can be seen from the following inequation:

$$\int_{T_1}^{T_1+\Delta T} I_o \cdot e^{-\frac{t}{\tau}} dt - \int_{T_1+\Delta T}^{T_1+2\Delta T} I_o \cdot e^{-\frac{t}{\tau}} dt > \theta;$$

$$T_1 > 0; \Delta T > 0;$$

Modified, alternating, phase-sensitive rectification in accordance with the following relationship represents a surprisingly simple possibility for eliminating the influence of crosstalk and the influence of D.C. drifts:

$$\int_{T_1}^{T_2} I_o \cdot e^{-\frac{t}{\tau}} dt - \int_{T_2}^{T_3} I_o e^{-\frac{t}{\tau}} dt + \int_{T_3}^{T_4} I_o \cdot e^{-\frac{t}{\tau}} dt = \theta$$

if the following relationship exists between $T_1$, $T_2$, $T_3$, $T_4$ and $\Delta T$:

$T_2 = T_1 + n_1 \Delta T;$ $T_3 = T_2 + n_2 \Delta T;$ $T_4 = T_3 + n_3 \Delta T;$ where $n_1 + n_3 = n_2.$ $n_1$, $n_2$ and $n_3$ are factors that permit differentiation between the respective periods of time as a multiple of interval of time $\Delta T$. Thus, rectification is performed alternately in different directions in a phase-sensitive manner during the relaxation phase of the fluorescence radiation. This produces rectification periods $n_1 \Delta T$ and $n_3 \Delta T$ in the one direction, or polarity, and $n_2 \Delta T$ in the other. The total durations of the rectification periods in each of the two directions must be identical.

For example, where $n_1 = 1;$ $n_2 = 3;$ $n_3 = 2;$ in the steady state, with an oscillation period that coincides with interval of time $T$, it is then found that:

$T = -\ln(\frac{1}{2}(\sqrt{5}-1)) \times \tau \approx 0.481 \times \tau.$

Other combinations of $n_1$, $n_2$ and $n_3$ are also possible, whereby the condition must be observed that $n_1 + n_2 = n_3$. In the case of signals which relax in a strictly monotonous manner, it would be necessary to appropriately adapt clock pulse relationships $n_1:n_2:n_3$.

Figure 1:
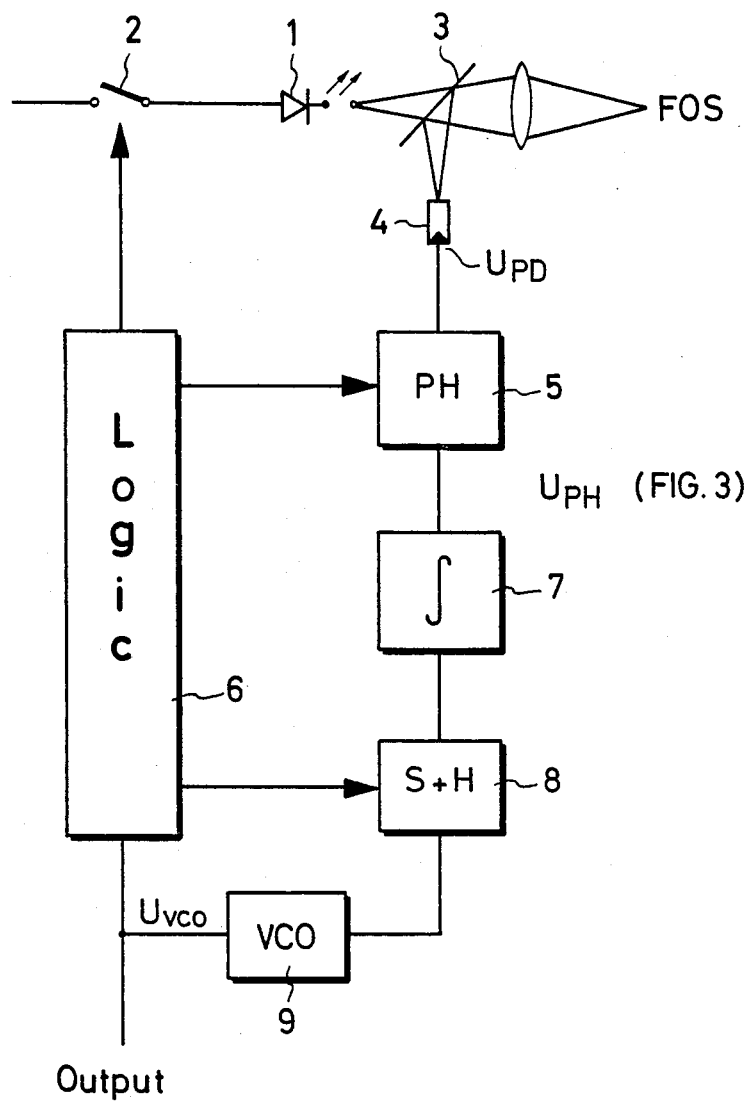
FIG. 1 shows a block schematic diagram of an apparatus for measurement of the fluorescence relaxation period of a fluorescent substance.

Referring now to the drawings, where like reference numerals designate like parts throughout the several views, FIG. 1 shows an example of the basic design of a fiber optic temperature sensor, in which the luminescence relaxation period is analyzed through the employment of alternating, phase-sensitive rectification, without sophisticated measures for suppression of crosstalk in the excitation channel.

A light emitting diode (LED) 1 is supplied periodically with operating voltage by means of a switch 2. Through optical means that are not described in more detail, for example, the radiation that is emitted from LED 1 is coupled into an optical waveguide, to one end of which a luminescent substance is applied. Optical means, optical waveguide and luminescent substance correspond to the arrangement that is illustrated in German Disclosed Patent Application No. 3,202,089, for example. The luminescent light that is radiated from the substance is advanced to a photoelectric receiver 4, e.g. a photodiode, via the optical waveguide and a radiation divider 3.

Figure 2:
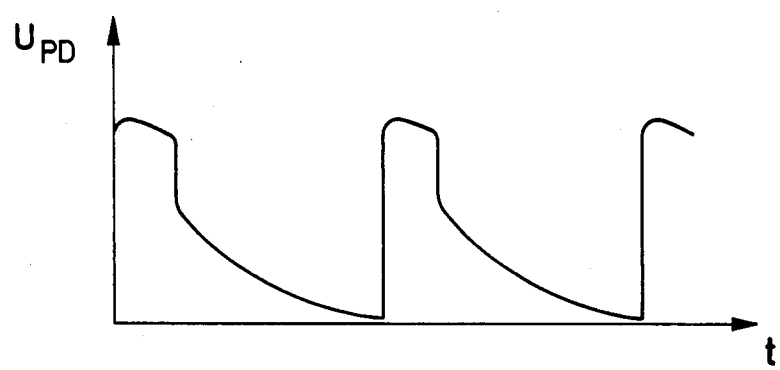
FIG. 2 shows a time diagram of the signals at the output of a photoelectric receiver of the apparatus according to FIG. 1.

The signal $U_{PD}$ that is illustrated in FIG. 2 is available at the output of photoelectric receiver 4. This signal then enters a phase-sensitive rectifier 5, which is controlled by a logic circuit 6, which also controls switch 2, which is preferably of contactless design. Phase-sensitive rectifier 5 is followed by an integrator 7, to which a scan and hold circuit 8 is connected, which is also controlled by means of logic circuit 6. Connected with scan and hold circuit 8 is the control input of a voltage controlled oscillator (VCO) 9, whose output is connected to an input of logic circuit 6. Logic circuit 6 thus completes a control circuit, whose control parameter is the frequency of the oscillation of the radiation that is influenced by the VCO, which serves as the control element.

Figure 3:
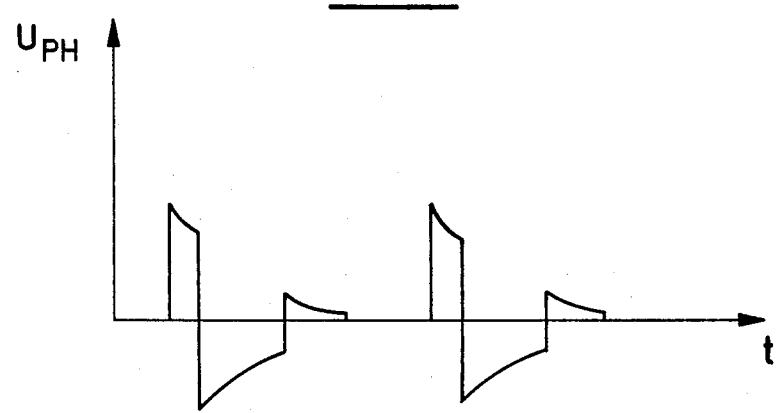
FIG. 3 shows a time diagram of the signals at the output of a phase-sensitive rectifier according to FIG. 1.
Figure 4:
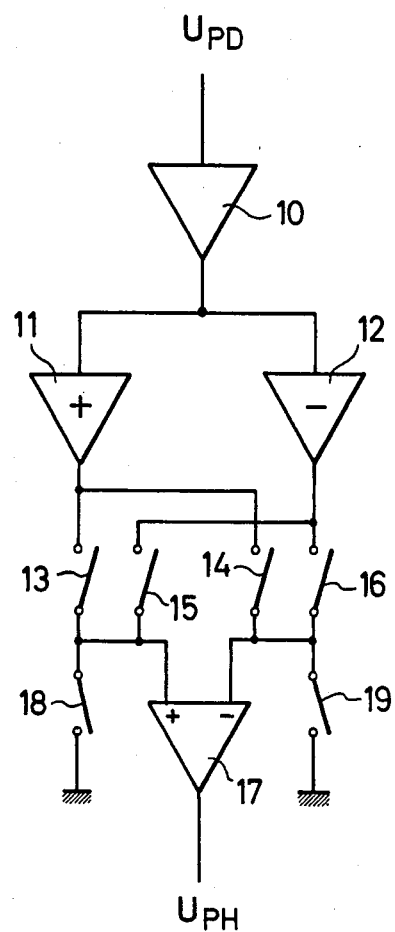
FIG. 4 shows the design of the circuitry of a phase-sensitive rectifier.

FIG. 4 shows the basic design of phase-sensitive rectifier 5. The output signal $U_{PD}$ from photoelectric receiver 4 is applied to the input of a preamplifier 10, whose output supplies a non-inverting amplifier 11 and an inverting amplifier 12. The output of non-inverting amplifier 11 is connected with two, preferably contactless switches 13, 14. Connected to the output of inverting amplifier 12 are two, preferably contactless switches 15, 16. Switches 13, 15 are connected with the non-inverting input of a differential amplifier 17, whose inverting input is connected with switches 14, 16. The non-inverting and the inverting inputs of differential amplifier 17 can each be applied to a grounding potential by means of switches 18, 19 respectively. Preamplifier 10 is a low-noise transimpedance amplifier. Signal $U_{PH}$, whose curve over time is illustrated in FIG. 3, is available at the output of differential amplifier 17. Switches 13 through 16 and 18, 19 are controlled by logic circuit 6. Switches 18, 19 are closed during the excitation phase. Switches 18, 19 are open during the relaxation phase. The closing time of switch 2 stipulates the duration of the excitation pulse.

As opposed to phase-sensitive rectification, with equally long, directly sequential addition and subtraction phases, with which zero balancing is not possible within the control circuit outside the excitation phase in the case of a strictly monotonous received signal $U_{PD}$ following integration of the output signal of the phase-sensitive rectifier $U_{PH}$, according to the present invention, this zero balancing is achieved in that an addition and a subtraction phase of differing lengths are again followed by an addition phase, whereby only the total duration of the two addition phases coincides with the duration of the subtraction phase, a condition that is required for elimination of D.C. drifts of input signal $U_{PD}$. The respective durations of the addition and subtraction phases are determined by the position of switches 13 through 16 and 18, 19, which are controlled by a logic circuit. In the case of a signal having simple exponential relaxation, a clock pulse ratio of 1:3:2 would be suitable. However, the present invention is not restricted to this type of signal, but also permits analysis of more complex monotonously relaxing signals through appropriately adapted clock pulse relationships $n_1:n_2:n_3$.

Figure 5:
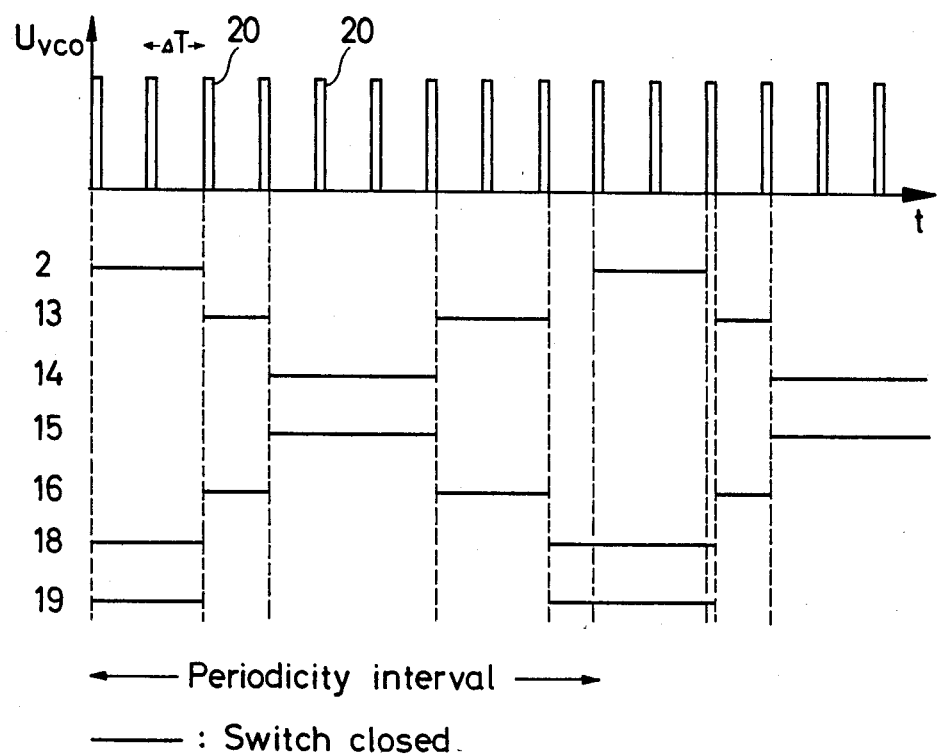
FIG. 5 shows a time diagram of control signals for switches in the phase-sensitive rectifier.

FIG. 5 shows an example of the positions of switches 13 through 16 and 18, 19, which are controlled by logic circuit 6, for the above-mentioned combination of $n_1=1$, $n_2=3$ and $n_3=2$ in a time diagram. During the excitation phase (switch 2 closed), the inputs of differential amplifier 17 are applied to zero potential by means of switches 18 and 19. Following phase-sensitive rectification, signal $U_{PH}$ is integrated in integrator 7 and then, during the excitation phase, assumed by scan and hold circuit 8, whose output signal controls voltage controlled oscillator (VCO) 9. In the steady state, the oscillation period $\Delta T$ is proportional to the relaxation period $\tau$. The interrelationship that exists between $\Delta T$ and $\tau$ is determined by clock pulse combination $n_1$, $n_2$ and $n_3$. For the above-indicated example, where $n_1=1$, $n_2=3$ and $n_3=2$, it will be found that $\Delta T \approx 0.481 \times \tau$.

In FIG. 5, the pulses from voltage controlled oscillator 9 are denoted 20.

Switches 13 and 16, on the one hand, and 15 and 14, on the other, are either simultaneously open or closed. After switches 18, 19 open, switches 13, 16 are first closed for the rectification period that is determined by $\Delta T$. Switches 13, 16 are then opened, while switches 15, 14 are closed for the rectification period that is determined by $n_2 \times \Delta T$. Switches 15, 14 are then opened, with switches 13, 16 again being closed for the rectification period that is determined by $n_3 \times \Delta T$. An excitation phase then commences when switch 2 closes.

In logic circuit 6, a counter which receives clock pulses from VCO 9 is preferably employed in conjunction with a demultiplexer in order to control the analog CMOS switch. In the case of the above-indicated clock pulse combination, the counter is reset after every eight clock pulses. It is also practical for logic circuit 6 to be able to be implemented with a $\mu P$.

The oscillation circuit is completed by means of logic circuit 6. Logic circuit 6 scales the frequency of voltage controlled oscillator 9, which oscillates at a higher frequency, for example, down to the frequency of the oscillation, which consists of an excitation phase and a relaxation phase, that is definitive for the closing time and the opening time of switch 2. The closing times of switches 13, 16 and 14, 15 each stipulate a rectification period, with one polarity being determined by switches 13, 16 and the other by switches 14, 15.

The output signal from integrator 7 is inputted to scan and hold circuit 8 at the end of the last phase-sensitive rectification period in a relaxation phase.

The rectification periods extend over at least the duration of one oscillation, i.e. oscillation period $\Delta T$. Rectification periods that are longer than the oscillation period of VCO 9 extend over multiples of these oscillation periods.

Figure 6:
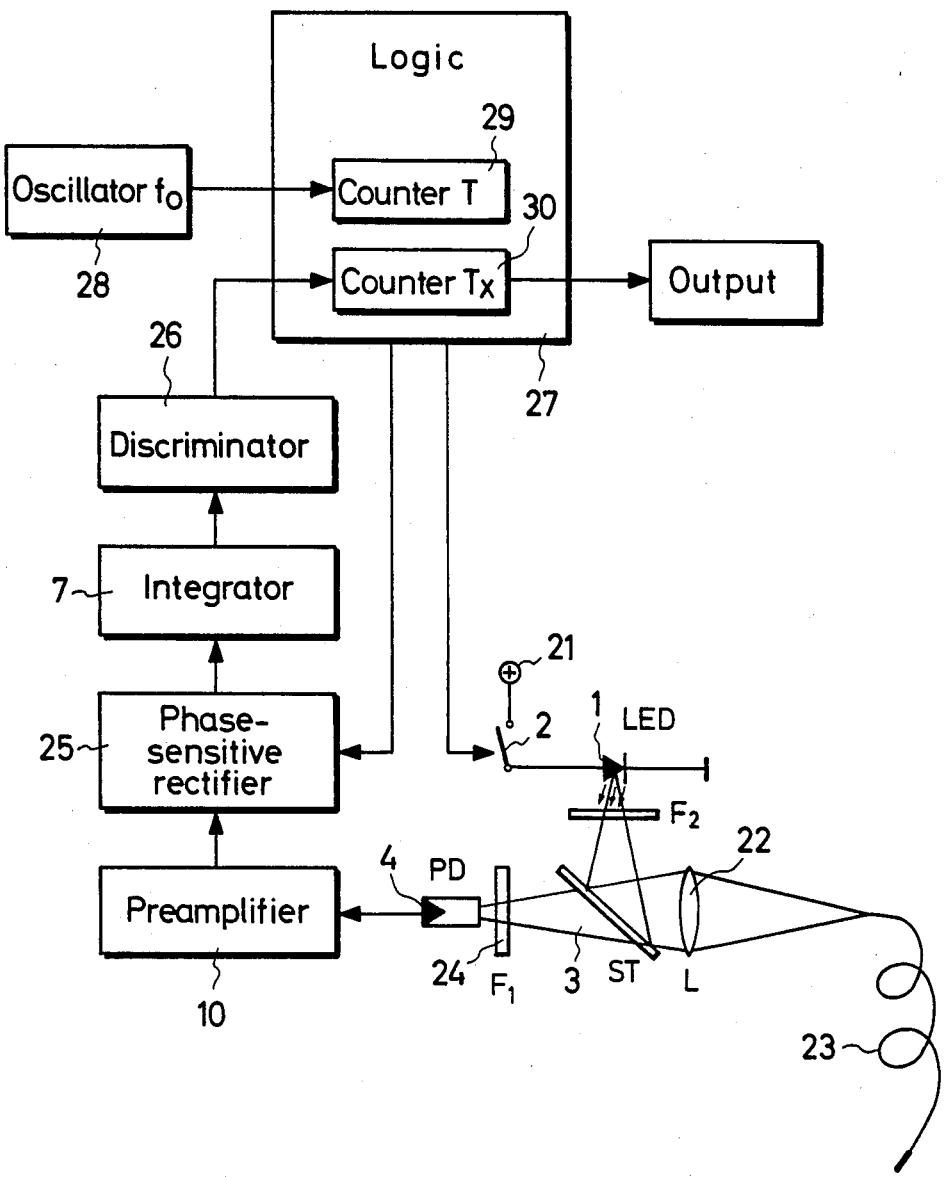
FIG. 6 shows a circuit diagram of another embodiment of an apparatus for measurement of the fluorescence relaxation period of a fluorescent substance.

Instead of the apparatus that was illustrated in FIG. 1, it is also possible to employ the apparatus that is shown in FIG. 6. Like the apparatus according to FIG. 1, the apparatus according to FIG. 6 also includes a light emitting diode 1 and a switch 2 which controls light emitting diode 1, with diode 1 being connected with an operating voltage, i.e. with a pole 21 of a voltage source, when switch 2 is actuated. The radiation that is emitted by diode 1 is coupled into an optical waveguide 23 through optical means 22; applied to the other end of optical waveguide 23 is a luminescent substance, which preferably consists of a sensor crystal of $Cr^{3+}:Y_3Al_5O_{12}$ or $Cr^{3+}:Al_2O_3$. It is practical for crystals to be employed that are doped with isoelectric impurities $V^{2+}$, $Cr^{3+}$ or $Mn^{4+}$. By means of combined doping with trivalent ions from the rare earth group, it is possible to achieve a luminescence relaxation period that is greatly dependent upon temperature as a result of the energy transfer between the different rare earth ions (e.g. $Nd^{3+}$ and $Yb^{3+}$), although the relaxation periods of the individual, isolated rare earth ions do not display any pronounced temperature dependency.

The radiation that emanates from the luminescent substance is advanced through optical waveguide 23, optical means 22 and a radiation divider 3, as well as through a filter 24, to a photoelectric receiver 4, which is followed by a preamplifier 10. Preamplifier 10 is preferably a constituent part of the phase-sensitive rectifier, as is illustrated in FIG. 4. In order to enhance understanding, FIG. 6 again schematically illustrates a phase-sensitive rectififer 25, which then does not include preamplifier 10. Rectifier 25 supplies an integrator 7, which is followed by a discriminator 26, which outputs sign-dependent binary signals, e.g. $\pm 1$, as a function of the polarity of the input signals, for example. A logic circuit 27 is connected with discriminator 26; in addition, logic circuit 27 is also supplied from an oscillator 28, which generates a sequence of clock pulses of constant frequency $f_o$ or virtually constant frequency. The clock pulses are applied to the counting inputs of a first counter 29 and a second counter 30, which is connected to an output circuit 31, at which a value is available that corresponds to the physical parameter. Logic circuit 27 controls the switches of phase-sensitive rectifier 25, i.e. switches 13, 14, 15, 16, 18 and 19 and switch 2, in the manner shown in FIG. 7. There is a fixed periodicity interval $T'_4$, at the end of which counter 29 is reset. The excitation phase is denoted $T'_1$. Excitation phase $T'_1$ is followed by a pause $T'_2$, during which switch 2 is open, while switch 17 and 19 are closed, as they also are during the excitation phase. Pause $T'_2$ is followed by an integration period, during which positive integration takes place.

In the method that is practiced with the arrangement according to FIG. 4, the excitation phase time is also present, although it is not expressly specified. Above-mentioned time $T_1$ is a pause that corresponds to pause $T_2$ in the arrangement according to FIG. 6. In the arrangement that is illustrated in FIG. 6, above-indicated time $T_2$ for positive integration corresponds to a time $T_2'+T_x$. Above-mentioned time $T_3$ for negative integration corresponds to a time $T_2'+T_x+T_3'$. In the case of the above-described practical example, this is followed by a time $T_4$ for positive integration, which corresponds to time $T_2'+2T_3'$ in accordance with the arrangement that is illustrated in FIG. 6. The arrangement according to FIG. 6 operates with precisely stipulated period $T_4'$.

The apparatus that is illustrated in FIG. 6 operates in the following manner:

The logic circuit effects control with the aid of oscillator 28, which oscillates at a fixed frequency $f_o$, and counter 29, which is reset again at the end of periodicity interval $T_4'$, by comparing the counter value, having stipulated values $T_1'$, $T_2'$, $T_3'$ and $T_4'$, with variable value $T_x$, which is formed in counter 30, the position of the switches of phase-sensitive rectifier 25, and thus the excitation, pauses and rectification (cf. FIG. 7), as well as of switch 2. A regulating circuit is completed in a highly simple manner in that parameter $T_x$ is increased or decreased by a value of 1, in accordance with the sign of the voltage at the output of integrator 7, upon completion of the integration phase, which is determined at discriminator 26. In the case of three rectifying periods, the times at which the rectifications are reversed are set in such a manner that the total of the integrals equals zero.

The count of counter 29 is increased by clock pulses of uniform frequency $f_o$, where $f_o=(\Delta/\Delta T)$. When count $n_4=T_4'/\Delta T$ is reached, which corresponds to period duration $T_4'$, the counter is reset to a value of zero. The count of counter 29 is compared with the count of counter 30 in order to set switches 13, 14, 15, 16, 18, 19. Relationships $n_1=T_1'/\Delta T$, $n_2=T_2'/\Delta T$, $n_3=T_3'/\Delta T$ and $n_x=T_x/\Delta T$ apply for counts $n_1$, $n_2$, $n_3$ and $n_x$.

The excitation phase corresponds to a count of $0 < n < n_1$, the pauses correspond to a count of $n_1 < n < n_2$ or $n_2+2n_3 < n < n_4$. Positive integration is performed as long as the count satisfies the condition where $n_2 < n < n_2+n_x$ or $n_2+n_x+n_3 < n < n_2+2n_3$, while negative integration is performed if count $n_2+n_x < n < n_2+n_x+n_3$.

In the case of the arrangement that is illustrated in FIG. 6, the count of counter 30 is altered at the end of each period $T_4'$ as a function of the sign of the output voltage of integrator 7 if frequency $f_o$ remains uniform and period $\Delta T$ thus remains constant. In the simplest case, count $n_x$ is increased by a value of 1 if the output voltage of integrator 7 is positive, while it is decreased by a value of 1 in the event of a negative output voltage. Consequently, adaptation is effected throughout the duration of the positive and negative integration periods where period $T_4'$ remains uniform. There is a clear interrelationship between the count at which the rectification is reversed in each instance and the relaxation period. In order to improve dynamic behavior, the regulating concept can be replaced by the following adaptive regulating concept.

Better regulating behavior can be achieved by means of the adaptive regulating concept, in which the number S of preceding periods determines the change $\Delta n_x$ of count $n_x$ of counter 30 without any change in the polarity of the integrator output voltage. Thus, for example, the count is altered in the following manner for the following number of periods S:

$S = 1$    $\Delta n_x = \pm 1$
$S = 2$    $\Delta n_x = \pm 2$
$S = 3$    $\Delta n_x = \pm 5$
$S = 4$    $\Delta n_x = \pm 10$.

The count parameter $T_x$ that is obtained thereby is a clear function of the relaxation period and can easily be converted if there is a known interrelationship between the relaxation period and the physical parameter that is to be measured.

The values for clock pulse frequency $f_o$ and parameters $T_1'$, $T_2'$, $T_3'$ and $T_4'$ are a function of the relaxation period and the required resolution (cf. example).

The pauses are employed for suppression of measurement errors as a result of the finite rise time of the preamplifier.

Logic circuit 27 can be implemented by means of discrete components, e.g. counters, comparators and logic gates, or with the aid of a microprocessor.

Preferred values are indicated in the following example:

Relaxation period: $\tau 200$ $\mu S$ − 2 ms
Clock pulse frequency: $f_o = 10$ MHz
Clock pulse period: $\Delta T$, of oscillator 28 = 0.1 $\mu S$
Excitation phases: 1 ms; $n_1 = 10,000$
Pause: 50 $\mu S$; $n_2 = 10,500$
Integration period: 1 ms; $n_3' = 10,000$   $n_4 = 31,000$
Resolution when $\tau = 200$ $\mu S$
$n_x = \pm 1 = \dfrac{\Delta \tau}{\tau} = \pm 8 \times 10^{-4}$
Resolution when $\tau = 2$ ms
$n_x = \pm 1 = \dfrac{\Delta \tau}{\tau} = \pm 18 \times 10^{-4}$.

The methods that are described above operate independently of the D.C. voltage at the output of preamplifier 10; i.e. A.C. coupling can be employed, with which the errors that are inherent in D.C. coupling can be avoided.

In the case of simple, exponentially relaxing signals, transmit time effects that occur with optical waveguide links of differing lengths can not affect the measurement, and thus the analysis (for example: 1 km optical waveguide=10 $\mu$s delay).

Figure 8A:
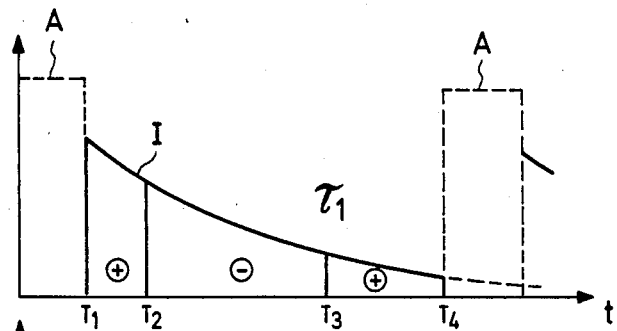
FIGS. 8a through 8d show time diagrams of the integrator output signals for various luminescence relaxation periods for each of the arrangements illustrated in FIGS. 1 and 6.
Figure 8B:
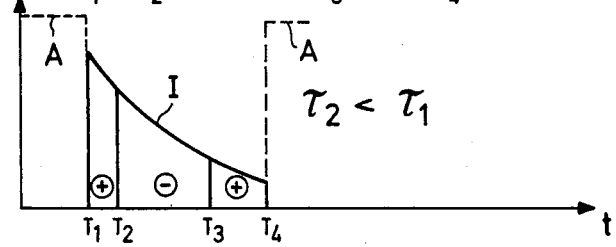
Figure 8C:
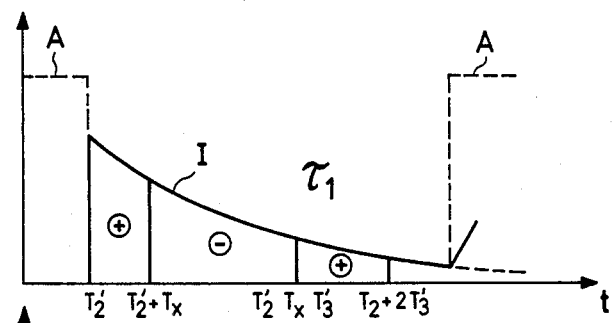
Figure 8D:
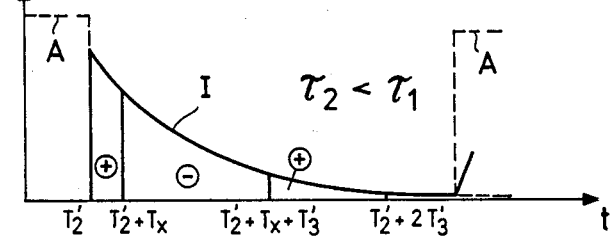

FIG. 8a shows excitation pulses (dashed) in the ordinate and the integrator output signal I as a function of time t, which is shown in the abscissa, for a first luminescence relaxation period $\tau_1$. In FIG. 8b, integrator output voltage I is shown in the ordinate as a function of time t in the abscissa for luminescence relaxation period $\tau_2 < \tau_1$. Times $T_1$, $T_2$, $T_3$ and $T_4$ are shown in both figures, with positive integration being denoted by means of a "+" and negative integration by means of a "−" in each case. It can be seen that the period $T_1$ to $T_4$ is also smaller where $\tau_2 < \tau_1$. In FIGS. 8c and d, in the same manner, integrator output signals 1 are shown in the ordinate and time t in the abscissa for both luminescence relaxation periods $\tau_1$ and $\tau_2$, with times $T_2'$, $T_3'$ and $T_x$ being entered on the abscissa along with a reference to the polarity of the integration. As can be seen from FIGS. 8c and 8d, there is a change in the relationships of the positive and negative integration periods with uniform $T_2'+2T_3'$.

In the arrangement shown in FIG. 6, the relative duration of at least two rectification periods in different directions is employed as the regulating parameter and is influenced in such a manner that the result of the integration will be as small as possible, for instance zero, at the end of the period of an oscillation.

It is also possible to alter all three rectification periods.

E.g.: Positive rectification where $n_2 < n < n_2 + n_x$ or
$n_2 + 4n_x < n < n_2 + 6n_x$,
Negative rectification where $n_2 + n_x < n < n_2 + 4n_x$
Pause where $n_2 + 6n_x < n < n_4$.

The present invention has been described above on the basis of preferred practical examples thereof. Obviously, many modifications and variations of the present invention are possible in the light of the above teachings. It should therefore be understood that, within the scope of the appended claims, the present invention may be practiced otherwise than as specifically described. In particular, individual characteristics of the invention can be employed individually or in combination one with the other.

What is claimed is:

1. A method for measuring the fluorescence relaxation period of fluorescent radiation from a fluorescent substance having a fluorescence relaxation period dependent upon a physical parameter, said method comprising the steps of:
   repeatedly subjecting the substance to excitation radiation in the form of oscillations from an oscillator of a regulating circuit having a regulating parameter corresponding to the physical parameter during time intervals in an excitation phase to produce fluorescence radiation from the substance during a relaxation phase;
   generating a radiation output signal representative of the fluorescence radiation from the fluorescent substance;
   alternately, only during the relaxation phase, phase-sensitively rectifying the radiation output signal in two different polarities with the total time of rectification in each polarity being equal to provide rectified output signals in each of said two polarities;
   integrating the rectified output signals and providing integrated signals therefrom in said two polarities; and
   controlling the voltage controlled oscillator according to a summation of the integrated signals in each polarity to control the excitation radiation.

2. The method according to claim 1, wherein said step of phase-sensitively rectifying the radiation output signal comprises phase-sensitively rectifying the output signal in the first of said polarities for a first predetermined time, phase-sensitively rectifying the output signal in the second of said polarities for a second predetermined time, and phase-sensitively rectifying the output signal in the first of said polarities for a third predetermined time.

3. The method according to claim 1, further comprising the steps of pausing without performing rectification after said excitation phase and after rectification of the radiation output signal.

4. A method for measuring the fluorescence relaxation period of fluorescence radiation from a fluorescent substance having a fluorescence relaxation period dependent upon a physical parameter, said method comprising the steps of:
   repeatedly subjecting the substance to excitation radiation in the form of oscillations from an oscillator of a regulating circuit having a regulating parameter corresponding to the physical parameter during time intervals in an excitation phase to produce fluorescence radiation from the substance, said oscillations having substantially uniform frequency;
   generating a radiation output signal representative of the fluorescence radiation from the fluorescent substance;
   alternately, only during the relaxation phase, phase-sensitively rectifying the radiation output signal in two different polarities to provide rectified output signals in two corresponding polarities;
   integrating the rectified output signals and providing integrated signals in said two polarities; and
   controlling the relative durations of rectification in each polarity so that a summation of the integrated signals in two polarities substantially equals zero to determine the regulating parameter corresponding to the physical parameter.

5. The method as claimed in claim 4, wherein the durations of phase-sensitive rectification in each of said polarities are equal.

6. The method according to claim 4, wherein said step of phase-sensitively rectifying the radiation output signal comprises phase-sensitively rectifying the output signal in the first of said polarities for a first predetermined time, phase-sensitively rectifying the output signal in the second of said polarities for a second predetermined time, and phase-sensitively rectifying the output signal in the first of said polarities for a third predetermined time.

7. The method according to claim 4, further comprising the steps of pausing without performing the rectification after said excitation phase and after rectification of the radiation output signal.

8. The method as claimed in claim 4, wherein said step of controlling the relative durations of rectification in each polarity comprises counting substantially uniform clock pulses during an oscillation period of said oscillator to obtain a clock pulse count, comparing said clock pulse count with stipulated values for the excitation phase and the durations of rectification in each polarity, and generating control signals for alternatively increasing or decreasing the durations of rectification in each polarity as a function of a positive or negative result of said integrating step, based upon said comparing step.

9. The method as claimed in claim 8, comprising discriminating said integrated signals in said two polarities by a discriminator and altering the durations of rectification in each polarity as a function of a number of preceding periods of said oscillator without changing the output of said discriminator.

10. An apparatus for measuring the fluorescence relaxation period of fluorescence radiation from a fluorescent substance having a fluorescence relaxation period dependent upon a physical parameter, said apparatus comprising:
    means for repeatedly subjecting a substance to excitation radiation during time intervals in an excitation phase to produce fluorescence radiation from the substance during a relaxation phase;
    a photoelectric receiver for receiving the fluorescence radiation from the fluorescent substance and providing a radiation output signal indicative thereof;
    a phase-sensitive rectifier receiving the radiation output signal for alternately, only during the relaxation phase, phase-sensitively rectifying the radiation output signal in two different polarities with the total time of rectification in each polarity being equal to provide rectified output signals in each of said two polarities, said rectifier including a differential amplifier having an inverting input, a non-inverting input and an output, and a plurality of switches for selectively connecting said inputs of said amplifier to said photoelectric receiver or, during the excitation phase, to a reference potential;
    an integrator connected to said rectifier for integrating the rectified output signals and providing integrated signals therefrom in said two polarities; and
    a regulating circuit having a regulating parameter corresponding to the physical parameter, said regulating circuit including a voltage controlled oscillator responsive to a summation of the integrated signals for controlling said excitation radiation, a scan and hold circuit connecting said oscillator to said integrator, and a logic circuit for controlling said plurality of switches for said rectifier.

11. The apparatus according to claim 10, wherein said phase-sensitive rectifier rectifies the radiation output signal for a duration equalling a multiple of the oscillation period of said voltage controlled oscillator.

12. The apparatus according to claim 10, wherein said phase-sensitive rectifier further comprises a preamplifier having an input connected to the output of said photoelectric receiver and a non-inverting amplifier and an inverting amplifier having inputs connected to the output of said preamplifier, and said switches of said rectifier comprise a first pair of switches for selectively connecting said outputs of said non-inverting amplifier and said inverting amplifier to said inverting input of said differential amplifier, a second pair of switches for selectively connecting said outputs of said non-inverting amplifier and said inverting amplifier to said non-inverting input of said differential amplifier, and a third pair of switches for selectively connecting said inputs of said differential amplifier to ground, said reference potential being ground.

13. An apparatus for measuring the fluorescent relaxation period of fluorescence radiation from a fluorescent substance having a fluorescence relaxation period dependent upon a physical parameter, said apparatus comprising:

means for repeatedly subjecting the substance to excitation radiation in the form of oscillations having substantially uniform frequency during time intervals in an excitation phase to produce fluorescence radiation from the substance;

a photoelectric receiver for receiving the fluorescence radiation from the fluorescent substance and providing a radiation output signal indicative thereof;

a phase-sensitive rectifier receiving the radiation output signal for alternatively, only during the relaxation phase, phase-sensitively rectifying the radiation output signal in two different polarities to provide rectified output signals in each of said two polarities, said rectifier including a differential amplifier having an inverting input, a non-inverting input and an output, and a plurality of switches for connecting said inputs of said amplifier to said photoelectric receiver or, during the excitation phase and during predetermined pauses, for connecting said inputs to a reference potential;

an integrator connected to said rectifier for integrating the rectified output signals and providing integrated signals in said two polarities; and a regulating circuit having a regulating parameter corresponding to the physical parameter and determined by the relative durations of rectification in each of said polarities; said regulating circuit including a discriminator connected to said integrator for receiving the integrated signals therefrom and a logic circuit connecting said discriminator to an output, said logic circuit having a counter for counting substantially uniform frequency clock pulses, said logic circuit comparing the count of said counter with predetermined values and controlling said switches of said rectifier to set the relative durations of rectification in each polarity so that a summation of the integrated signals in said two polarities substantially equals zero.

14. The apparatus according to claim 13, wherein said phase-sensitive rectifier further comprises a preamplifier having an input connected to the output of said photoelectric receiver and a non-inverting amplifier and an inverting amplifier having inputs connected to the output of said preamplifier and said switches of said rectifier comprise a first pair of switches for selectively connecting said outputs of said non-inverting amplifier and said inverting amplifier to said inverting input of said differential amplifier, a second pair of switches for selectively connecting said outputs of said non-inverting amplifier and said inverting amplifier to said non-inverting input of said differential amplifier, and a third pair of switches for selectively connecting said inputs of said differential amplifier to ground, said reference potential being ground.

* * * * *